United States Patent
Dal Farra et al.

(10) Patent No.: US 8,012,938 B2
(45) Date of Patent: Sep. 6, 2011

(54) DERMATOLOGICAL AND/OR COSMETIC COMPOSITION CONTAINING POLYPEPTIDES

(75) Inventors: Claude Dal Farra, Opio (FR); Nouha Domloge, Valbonne (FR); Jean-Marie Botto, Valbonne (FR)

(73) Assignee: ISP Investments Inc., Wilmington, DE (US)

(*) Notice: Subject to any disclaimer, the term of this patent is extended or adjusted under 35 U.S.C. 154(b) by 1129 days.

(21) Appl. No.: 10/589,863

(22) PCT Filed: Dec. 23, 2004

(86) PCT No.: PCT/FR2004/003357
§ 371 (c)(1),
(2), (4) Date: Aug. 17, 2006

(87) PCT Pub. No.: WO2005/089706
PCT Pub. Date: Sep. 29, 2005

(65) Prior Publication Data
US 2008/0171076 A1    Jul. 17, 2008

(30) Foreign Application Priority Data
Feb. 18, 2004 (FR) ..................... 04 01593

(51) Int. Cl.
*A61K 38/00* (2006.01)
*A61K 38/08* (2006.01)
*A61K 38/10* (2006.01)
*A61K 8/00* (2006.01)
*C07K 7/00* (2006.01)
*C07K 7/06* (2006.01)
*C07K 7/08* (2006.01)

(52) U.S. Cl. ...... 514/21.6; 514/1.1; 514/18.6; 514/18.8; 514/21.5; 530/300; 530/327; 530/328

(58) Field of Classification Search .................. None
See application file for complete search history.

(56) References Cited

U.S. PATENT DOCUMENTS
2003/0036646 A1    2/2003  Ni et al.

FOREIGN PATENT DOCUMENTS

| WO | 00/02577 | 1/2000 |
|---|---|---|
| WO | 00/06087 | 2/2000 |
| WO | 02/07754 | 1/2002 |
| WO | 2004/059001 | 7/2004 |

OTHER PUBLICATIONS

Carbopol Ultrez 10 from http://www.homecare.noveon.com/products/carbopol/ultrez_10.asp, pp. 1-2. Accessed Mar. 12, 2009.*
Definition of derivative from http://cancerweb.ncl.ac.uk/omd/about.html, pp. 1-5, Accessed Jul. 7, 2005.*
Rudinger J, "Characteristics of the amino acids as components of a peptide hormone sequence," Peptide Hormones, JA Parsons, Edition, University Park Press, Jun. 1976, pp. 1-7.*
Designing Custom Peptides from SIGMA Genosys, pp. 1-2. Accessed Dec. 16, 2004.*
Schinzel R and Drueckes P, "The phosphate recognition site of *Escherichia coli* maltodextrin phosphorylase," FEBS, Jul. 1991, 286(1,2): 125-128.*
Berendsen Herman JC, "A Glimpse of the Holy Grail?", Science, Oct. 23, 1998, 282:642-643.*
Voet Donald and Voet Judith G., Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problems and Tertiary Structure Prediction, K. Merc Jr. and S. Le Grand, Edition, 1994, 491-495.*
Bradley CM and Barrick M, "Limits of Cooperativity in a Structurally Modular Protein: Response of the Notch Ankyrin Domain to Analogous Alanine Substitutions in Each Repeat," J. Mol. Biol., 2002, 324: 373-386.*

* cited by examiner

Primary Examiner — Julie Ha
(74) Attorney, Agent, or Firm — Young & Thompson

(57) ABSTRACT

The present invention relates to the use of proteins of the UCP family, or UCP protein polypeptide or peptide fragments, as an active agent, alone or in association with at least one other active agent, in or for the preparation of a pharmaceutical and/or dermatological and/or cosmetic composition. The invention also relates to any composition containing the aforementioned active ingredient, as well as its use as a slimming agent.

23 Claims, No Drawings

SEQUENCE LISTING

```
<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 1

Pro Leu Asp Thr Ala Lys Val Arg Leu Gln
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Thr Glu Val Ala Lys Val Arg Phe Gln
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Thr Asp Val Ala Lys Val Arg Leu Gln
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Thr Glu Val Ala Lys Val Arg Leu Gln
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Thr Asp Val Ala Lys Val Arg Phe Gln
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Val Asp Val Val Lys Thr Arg Phe Ile
 1               5                  10

<210> SEQ ID NO 7
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Val Asp Val Val Lys Thr Arg Tyr Met
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Val Asp Val Val Lys Thr Arg Phe Met
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Val Asp Val Val Lys Thr Arg Tyr Ile
 1               5                  10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)
<223> OTHER INFORMATION: Xaa = any amino acid, and can be from 0 to 1
      amino acid
<220> FEATURE:
<221> NAME/KEY: misc_feature
<222> LOCATION: (2)
<223> OTHER INFORMATION: Xaa = any amino acid, and can be from 0 to 1
      amino acid
<220> FEATURE:
<221> NAME/KEY: misc_feature
<222> LOCATION: (4)
<223> OTHER INFORMATION: Xaa = Leu, Thr or Val
<220> FEATURE:
<221> NAME/KEY: misc_feature
<222> LOCATION: (5)
<223> OTHER INFORMATION: Xaa = Asp or Glu
<220> FEATURE:
<221> NAME/KEY: misc_feature
<222> LOCATION: (6)
<223> OTHER INFORMATION: Xaa = Leu, Thr or Val
<220> FEATURE:
<221> NAME/KEY: misc_feature
<222> LOCATION: (7)
<223> OTHER INFORMATION: Xaa = Ala or Val
<220> FEATURE:
<221> NAME/KEY: misc_feature
<222> LOCATION: (9)
<223> OTHER INFORMATION: Xaa = Leu, Thr or Val
<220> FEATURE:
<221> NAME/KEY: misc_feature
<222> LOCATION: (11)
```

```
<223> OTHER INFORMATION: Xaa = Leu, Phe or Tyr
<220> FEATURE:
<221> NAME/KEY: misc_feature
<222> LOCATION: (12)
<223> OTHER INFORMATION: Xaa = Gln, Ile or Met
<220> FEATURE:
<221> NAME/KEY: misc_feature
<222> LOCATION: (13)
<223> OTHER INFORMATION: Xaa = any amino acid, and can be from 0 to 1
     amino acid
<220> FEATURE:
<221> NAME/KEY: misc_feature
<222> LOCATION: (14)
<223> OTHER INFORMATION: Xaa = any amino acid, and can be from 0 to 1
     amino acid

<400> SEQUENCE: 10

Xaa Xaa Pro Xaa Xaa Xaa Xaa Lys Xaa Arg Xaa Xaa Xaa Xaa
  1               5                  10
```

DERMATOLOGICAL AND/OR COSMETIC COMPOSITION CONTAINING POLYPEPTIDES

FIELD OF THE INVENTION

The invention relates to the pharmaceutical field, and in particular, the fields of dermatology and cosmetology.

The present invention relates to the use of proteins of the UCP family, or polypeptide or peptic protein UCP fragments, as an active agent, alone or in association with at least one other active agent, in or for the preparation of a pharmaceutical and/or dermatological and/or cosmetic composition. The invention relates also to any composition containing the aforementioned active ingredient.

BACKGROUND OF THE INVENTION

The term "UCP" designates the family of "uncoupling proteins"; which are implicated in the uncoupling between the reoxidation of coenzymes and the phosphorylation of ADP in ATP at the level of mitochondria (Nicholls et al., Physiol. Rev., 64: 1-64, 1984).

To date, three proteins of this family have been identified: UCP-1, UCP-2 and UCP-3. UCP-1 was the first protein identified (Flax et al., FEBS Lett, 113: 299-303, 1980). It is an uncoupling protein present in brown adipose tissue (Cassard et al., Newspaper of Cell biochemistry, 43, 1990). This form of brown adipose tissue is well-known in small mammals, hibernating animals, and newborn mammals; it is a thermogenic organ which makes it possible to resist the cold by producing heat. The strong thermogenic activity of brown adipocytes comes from the presence of UCP-1. This protein dissipates part of the energy in the form of heat by an uncoupling between cellular respiration and ATP synthesis. Indeed, UCP-1 is a proton transporter present in the inner membrane of mitochondria. When the protein is activated, it catalyzes proton gradient dissipation through the membrane and short-circuits ATP synthase. Respiration, no longer coupled with ADP phosphorylation, becomes a purely thermogenic process. The uncoupling of respiration stimulates fat oxidation and generates heat.

In addition to UCP-1, two other uncoupling proteins, which are very close to UCP-1, have been identified: UCP-2 (Fleury et al., Nature Genetics, 15: 269, 1997), which one finds in a wide variety of tissues, such as the intestines, adipose tissues, muscles, the brain, and cells of the immune system; and UCP-3 (Boss O. et al., FEBS Lett, 1997), primarily located in skeletal muscles and brown adipose tissue.

These uncoupling proteins, especially UCP-2 and UCP-3, are proteins that are not well-known. However, studies have shown that they probably play a significant role in energy homeostasis (Klingenberg, J Bioenerg. Biomembr. 25: 447, 1993), noteworthy, in energy metabolism in general and in the control of the metabolic efficacy of food in particular.

The study of these proteins, and their encoding genes, involved in energy metabolism, have provided a new approach as well as new therapeutic targets making it possible to intervene in the regulation of energy metabolism in mammals. In particular, research has been undertaken in the development of drugs which would act, by gene therapy, on the absence or excess of UCP proteins. Up to today, on a therapeutical level, UCP proteins have only been considered potential targets in the domain of genetics, in order to treat dysfunctions or diseases related to obesity, diabetes, and hyperlipidemia, among others.

Thus, on a therapeutic level, only the use of active ingredients capable of acting on protein expression have been considered. Thus, patents JP2003113104 and JP2003113106 describe, for example, compositions made from plant extracts that are able to stimulate UCP protein expression in brown tissue adipocytes. UCP proteins have never been used, themselves, as an active ingredient.

SUMMARY OF THE INVENTION

In a quite surprising and unexpected way, the inventors have shown a therapeutic activity and, more specifically, a dermatological and cosmetic activity of these UCP proteins and/or these polypeptide or peptide fragments, particularly when these peptides and/or these peptide fragments are applied to the skin.

Specifically, the inventors have demonstrated a localized slimming effect when these UCP proteins and/or these peptide fragments are applied to the skin. More particularly, it was shown that these agents are able to reduce, eliminate, or prevent excess of subcutaneous fat. These agents thus open new therapeutic and cosmetic prospects.

Consequently, according to a first aspect, the present invention has as an aim the use of proteins of the UCP family, or peptide or polypeptide fragments of the UCP family, or biologically active derivatives, as an active agent, alone or in association with at least one other active agent, in or for the preparation of a pharmaceutical and/or dermatological and/or cosmetic composition.

Particularly, the invention relates to the use of proteins of the UCP family or peptide fragments of the UCP family or biologically active derivatives, as a slimming active agent, in or for the preparation of a dermatological and/or cosmetic composition.

Preferentially according to the present invention, the aforementioned protein peptide fragments of the UCP family are peptide fragments of which the number of amino acids ranges from 3 to 200, more particularly from 7 to 50. All these peptide fragments have a biological activity.

DETAILED DESCRIPTION OF THE INVENTION

Preferentially according to the invention, the peptide fragments are peptides of formula (I):

(AA)n-Pro-X1-X2-X1-X3-Lys-X1-Arg-X4-X5-(AA)n (I)
   (SEQ ID NO:10)

wherein:
X1=Leu, Thr, Val;
X2=Asp, Glu;
X3=Ala, Val;
X4=Leu, Phe, Tyr;
X5=Gln, Ile, Met;

and where (AA) is any particular amino acid or one of its derivatives, and n is a whole number ranging from 0 to 2.

According to a particularly advantageous method of embodiment of the invention, the peptide belonging to the UCP family is characterized in particular by the fact that it is selected from peptides corresponding to the ID NO sequence:

```
1) Pro Leu Asp Thr Ala Lys Val Arg    (SEQ ID NO: 1)
   Leu Gln

2) Pro Thr Glu Val Ala Lys Val Arg    (SEQ ID NO: 2)
   Phe Gln

3) Pro Thr Asp Val Ala Lys Val Arg    (SEQ ID NO: 3)
   Leu Gln
```

```
4) Pro Thr Glu Val Ala Lys Val Arg      (SEQ ID NO: 4)
   Leu Gln

5) Pro Thr Asp Val Ala Lys Val Arg      (SEQ ID NO: 5)
   Phe Gln

6) Pro Val Asp Val Val Lys Thr Arg      (SEQ ID NO: 6)
   Phe Ile

7) Pro Val Asp Val Val Lys Thr Arg      (SEQ ID NO: 7)
   Tyr Met

8) Pro Val Asp Val Val Lys Thr Arg      (SEQ ID NO: 8)
   Phe Met

9) Pro Val Asp Val Val Lys Thr Arg      (SEQ ID NO: 9)
   Tyr Ile
```

In addition, according to a highly preferred method of embodiment of the invention, the peptide fragment from the UCP family has as a sequence ID NO (1), i.e. the sequence Pro-Leu-Asp-Thr-Ala-Lys-Val-Arg-Leu-Gln (SEQ ID NO: 1).

The invention also relates to variant forms of these sequences and/or of these fragments. The expression "variant" indicates a polypeptide or a peptide that differs, for example, from the sequence of a reference peptide while keeping its essential properties. Generally, the differences are limited so that the sequences of the reference peptide and those of the variant are quite similar and, in some regions, identical.

Preferentially, the variant forms are those which vary from reference sequences by the substitution of chemically equivalent (or homologous) amino acids, that is, by the substitution of a residue with another possessing the same characteristics. Thus, classical substitutions take place between Ala, Val, Leu and Ile; between Ser and Thr; between the acid residues Asp and Gln; and between the basic residues Lys and Arg, or between the aromatic residues Phe and Tyr.

The expression "variant" indicates a polypeptide or a peptide that differs, for example, from the sequence of a reference peptide while keeping its essential properties. Generally, the differences are limited so that the sequences of the reference peptide and those of the variant are quite similar and, in some regions, identical. A variant peptide and a reference peptide may differ in their amino acid sequence by one or several substitutions, additions, or deletions in all the combinations.

UCP protein fragments of polypeptidic or peptidic nature, described in the present invention, also include the use of all biologically active fragments, or one of their analogues or variants. By the expression 'biologically active', one understands, as well, fragments which have an in vivo or in vitro activity characteristic of the activity of the active ingredient according to the invention, such as, for example, the slimming activities described previously.

In the invention, the term "amino acid" refers to any natural or unnatural organic acid having the formula (II):

—NHR—CR—C(O)—O    (II)

where each —R is independently selected from a hydrogen or an alkyl group having between 1 and 12 carbon atoms. Preferentially, at least an —R group of each amino acid is a hydrogen. The term "alkyl" refers to a carbon chain that can be linear or branched, substituted (mono- or poly-) or not substituted; saturated, mono-saturated (a double or triple bond in the chain), or poly-unsaturated (two or several double bonds, two or several triple bonds, one or several double bonds, and one or several triple bonds in the chain).

The term "peptide" indicates a sequence of two or several amino acids linked together by peptide bonds or by modified peptide bonds; and a polypeptide indicates a peptide of larger size. The term "peptide" refers to a natural or synthetic peptide of the invention as described above or at least any natural or synthetic peptide whose sequence is totally or partly constituted by the sequence of the peptide previously described.

It may be that, concerning issues of resistance to degradation, it is necessary to use a protected form of the peptide according to the invention. The form of protection must obviously be biologically compatible and must also be compatible with use in the cosmetic and pharmaceutical fields.

Many biologically compatible forms of protection can be considered, such as acylation or acetylation of the amino terminal end, or amidation or esterification of the terminal carboxyl end. Such forms are well known by those skilled in the art. Thus, the invention relates to the use as previously defined and is characterized by the fact that the peptide either is or is not in a protected form. Preferably, the protection used is either acylation or acetylation of the amino terminal group, or esterification or amidation of the terminal carboxyl end, or both of them. The amino acid derivatives and the peptide derivatives also relate to amino acids and peptides bound together by a pseudo-peptide bond. By the term "pseudo-peptide bond," we refer to all types of bonds likely to replace "classical" peptide bonds.

In the domain of amino acids, the geometry of the molecules is such that they can be theoretically presented as different optical isomers. There is indeed a molecular conformation of the amino acid (AA) such that it deviates to the right of the plane of polarization of the light (dextrorotatory conformation or D-aa), and a molecular conformation of the amino acid (aa) such that it deviates to the left of the plane of polarization of the light (levorotatory conformation or L-aa). Nature retained for the natural amino acids only levorotatory conformation. Consequently, a peptide of natural origin will be made up only of amino acids of type L-aa. However, chemical synthesis in a laboratory makes it possible to prepare amino acids having two possible conformations. From this basic material, it is thus possible to incorporate, during peptide synthesis, amino acids in the form of dextrorotatory or levorotatory optical isomers. Thus, the amino acids constituting the peptide according to the invention, can be under configuration L- and D-; in a preferential way, amino acids are in L configuration. The peptide according to the invention can be in L, D, or DL-configuration.

According to the invention, the peptides can be prepared using all appropriate methods. Thus, the peptides can be isolated peptides from peptides and proteins existing naturally, recombinant peptides, synthetic peptides, or peptides produced by a combination of these methods. Of course, the methods, in order to prepare the peptides according to the invention, are well known by one skilled in the art. Thus, the peptide according to the invention may be of natural or synthetic origin. Preferentially, according to the invention, the peptide is obtained by chemical synthesis.

According to an advantageous mode of embodiment of the invention, the abovementioned peptides are solubilized beforehand in one or several cosmetically or pharmaceutically acceptable solvents classically used by one skilled in the art, such as water, ethanol, propylene glycol, butylene glycol, dipropylene glycol, ethoxylated or propoxylated diglycols, cyclic polyols, vaseline, a vegetal oil, or any combinations of these solvents.

According to another advantageous mode of embodiment of the invention, the abovementioned peptides are solubilized beforehand in one cosmetic or pharmaceutical vector such as liposomes or adsorbed on powdery organic polymers, mineral supports like talcs and bentonites, and more generally solubilized in, or fixed on, any cosmetically or pharmaceutically acceptable vector.

It is of course obvious that the peptide according to the invention can be used alone or in association with at least one other active agent, in or for the preparation of a cosmetic and/or dermatological and/or pharmaceutical composition.

An essential aspect of the invention is the use of at least one protein of the UCP family, peptide or polypeptide fragments, or biologically active derivatives, in or for the preparation of a cosmetic and/or pharmaceutical composition for topical use particularly intended to act against cellulite and/or orange peel skin. The aforementioned peptides are advantageously used in order to reduce, eliminate, and/or prevent excess of subcutaneous fat.

More precisely, the present invention aims at using at least one protein of the UCP family, peptide fragments, or biologically active derivatives, as previously defined, as a slimming agent likely to be used particularly in the field of cosmetics. The invention relates to, in the same way, the use of peptides, such as those previously defined, as a slimming agent. According to a current preferred method of embodiment of invention, the slimming active agent is the peptide having (SEQ ID NO: 1).

These peptides can be used in or for the preparation of a cosmetic and/or pharmaceutical composition for topical use particularly intended to act against cellulite and/or orange peel skin. They are used in a more general manner in order to reduce, eliminate, or prevent excess of subcutaneous fat.

The hypodermis consists of large vacuolated cells or adipocytes which are almost entirely filled with triglycerides. This adipose tissue also has conjunctive tissue containing, among others things, particular fibroblasts and preadipocytes. This adipose tissue constitutes the largest energy storage of the body. It is capable of storing lipids in the form of triglycerides and releasing them in the form of fatty acids and glycerol. The lipid storages of our body are constantly renewed and an equilibrium exists that is continuously adapted to the energy needs of the body, between the phenomenon of lipolysis, which releases fatty acids, and the phenomenon of lipogenesis which stores them. If an imbalance sets in between these two phenomena in the body, the fatty acids are stored in adipocytes, whose volume and number increase: from this we can observe phenomena such as hypertrophy and hyperplasy of adipocytes. The excessive development of adipose mass can then result in modifications of the appearance of the skin, and even lead to an individual being overweight, or yet still, progress towards true obesity.

Cellulite is a particular configuration of adipose tissue, considered unaesthetic today. It refers to the dimpled and lumpy appearance of the skin which corresponds, in a diagrammatic way, with the increase of adipose tissue in certain areas of the body, in particular, in women, on the hips, thighs, buttocks, knees, and forearms. At an advanced stage of cellulite formation, the skin spontaneously takes on an "orange peel" or dimpled appearance, which is characterized by a succession of small bumps and depressions due to a traction of the skin towards deep tissues.

It has been noted that the peptides, according to the invention, or the composition containing them, have a very efficient action on adipocytes. Indeed, they significantly contribute to a decrease in the quantity of triglycerides contained in adipocytes of the hypodermis.

This phenomenon is probably due to a blocking of the phenomenon of lipogenesis, i.e. to a blocking of the process of triglyceride storage which leads to adipocyte hypertrophy. A control of lipogenesis, i.e. the reaction of triglyceride synthesis in adipocytes, makes it possible to avoid adipocyte hypertrophy as well as consecutive hyperplasy. Thus, when, in the course of adipocyte differentiation, the quantity of triglycerides present in the vacuoles does not increase, the volume of adipocytes and their number do not increase either. The skin thus regains, gradually, its "normal" appearance: cellulite tissue no longer develops, the orange peel effect on the skin is attenuated. The unsightly aspect of the body gradually diminishes.

The active ingredient, according to the invention, thus makes it possible to prevent the appearance of cellulite as well as to fight against its aggravation.

According to another aspect, the invention relates to a cosmetic and/or dermatological and/or pharmaceutical composition characterized by its containing, in an acceptable medium, as an active ingredient, proteins of the UCP family and/or polypeptide or peptide fragments of the UCP family, or peptides such as previously defined.

In an advantageous way the composition according to the invention contains one or more peptides chosen among peptides corresponding to SEQ ID NO:1 to SEQ ID NO:9. According to a particularly advantageous embodiment of the invention, the composition contains the peptide of sequence Pro-Leu-Asp-Thr-Ala-Lys-Val-Arg-Leu-Gln (SEQ ID NO:1). In a more general way, the composition, according to the invention, contains the active compound previously defined.

In the composition, according to the invention, the peptide can be a mixture of peptide derivatives and/or be made up of amino acid derivatives. It is clearly understood that the peptide according to the invention can be used alone or in association with at least one other active agent.

In particular, the invention relates to a cosmetic composition intended to obtain a slimming action, and/or intended to reduce, eliminate, or prevent excess subcutaneous adipose fat, characterized in that it includes an effective cosmetic amount of at least one of the peptides or polypeptides or protein fragments previously defined, in order to obtain the aforementioned slimming action and/or in order to reduce, eliminate, or prevent excess subcutaneous fat. The composition, according to the invention, is also advantageously intended to fight against cellulite and/or is intended to decrease the orange peel skin phenomenon or make it disappear.

The composition containing the peptide according to the invention can be a cosmetic or dermatological or pharmaceutical composition. Preferentially, according to the invention, the composition is a cosmetic composition, because it is intended to improve the appearance and the general cutaneous results of the individual who uses it. The composition according to the invention is preferentially a cosmetic and/or dermatological composition adapted to topical administration including a cosmetically or pharmaceutically acceptable medium.

It is quite obvious that the invention is addressed to mammals in general and more particularly to human beings.

As an example, the composition according to the invention can be applied locally to the zones of the face or the body to be slimmed, in particular on the hips, buttocks, thighs, stomach or the face. One of the many advantages of this invention is that it offers an effective topical treatment against adiposity while using "gentle" methods.

The effective quantity of active ingredient corresponds to the quantity necessary in order to obtain the desired result.

According to an advantageous mode of embodiment of the invention, the abovementioned peptide is present in the compositions of the invention at a concentration ranging from approximately 0.005 to 500 ppm (parts per million), and preferentially with a concentration ranging from approximately 0.1 to 50 ppm compared to the total weight of the final composition.

Whatever the form of the invention, the composition according to the invention can be injected or applied to the skin (on any cutaneous zone of the body), hair, nails or mucous membranes. According to the mode of administration, the composition according to the invention, can be in all the galenic forms normally used.

Preferentially, the compositions related to the invention are presented under a galenic form adapted for cutaneous topical administration. They cover all the cosmetic and dermatological forms. These compositions must contain an acceptable cosmetic or dermatological medium. That is to say, a medium that is compatible with skin, mucous membranes, hair, and nails.

These compositions can take the form of an aqueous, hydro-alcoholic, or oil solution; or the form of oil-in-water emulsions, water-in-oil emulsions, or multiple emulsions. They can also be used as creams, suspensions, or powders adapted for application to the skin, mucous membranes, lips, and/or hair and nails. These compositions can also be more or less fluid or solid and can take the form of creams, lotions, milks, serums, ointments, shampoos, gels, pastes, and mousse. They can also take a solid form like a stick, or they can be used on the skin or in aerosols. They can also be used as a skin care product and/or as make-up for the skin.

Moreover, these compositions can include all of the additives that are usually considered for use in this application including all the possible additives necessary for their formulation such as solvents, thickeners, diluents, antioxidants, colorants, solar filters, auto-tanning products, pigments, fillers, preservatives, perfumes, odor absorbers, pharmaceutical and cosmetic active ingredients, essential oils, vitamins, essential fatty acids, tensioactivators, filmogenic polymers, etc.

In all cases, one skilled in the art will carefully consider the selection of additives, as well as their proportions, so as not to compromise the advantageous properties of the composition relating to the invention. These additives can, for example, correspond to 0.01% to 20% of the total weight of the composition. When the composition according to the invention is an emulsion, the fatty phase can represent 5% to 80% of the weight, but preferably it would represent 5% to 50% of the weight with respect to the total weight of the composition. Emulsifiers or co-emulsifiers used in the composition will be selected from among those that are classically used in the domain under consideration. For example, they can be used in a proportion of 0.3% to 30% of the weight relative to the total weight of the composition. Of course, the person skilled in the art should select the complementary compounds for the composition, active or non-active, as well as the amounts of the complementary compounds in such a way that the advantageous properties of the composition will not be perceptibly altered by the envisioned addition.

According to the invention, we can add to the composition of the invention other active agents intended, among other things, for the treatment of cellulite and the 'orange peel skin' phenomenon. Preferentially, for the purpose of slimming, the composition according to the invention will contain, for example, advantageously, in addition to the active ingredient previously defined, an active promoting lipolysis.

The compositions, according to the present invention, can be applied notably as cosmetic or pharmaceutical compositions for the skin, mucous membranes, and/or semi-mucous membranes. The compositions can be applied as skin protection and/or as skin care products, or as an anti-wrinkle and/or an anti-aging composition, but above all they can be applied more particularly as a slimming and/or toning composition.

The toning and/or slimming composition can be applied locally to the zones of the face or body to slim, in particular, the hips, buttocks, thighs, stomach, or face. We can also envision other applications in the domain of combined compositions, for example, the combining of the abovementioned composition with other active agents.

The present invention also relates to a cosmetic care process in order to obtain a slimming lotion as well as a cosmetic process intended to reduce, eliminate, and/or prevent excess subcutaneous fat. This process is also intended to fight against cellulite and/or the 'orange peel skin' phenomenon. This process consists in applying, topically, on the related zones of the skin of the face and/or body, an effective amount of peptides, according to the invention, such as previously defined, or a composition, such as previously defined, containing them.

The invention's process of cosmetic treatment can be implemented in particular by applying the cosmetic compositions defined above, according to the technique of customary use of these compositions, for example: application of creams, gels, serums, lotions, milks, shampoos, or anti-solar compositions on the skin.

The particular modes of embodiment of this cosmetic treatment process also result from the preceding description.

Other advantages and characteristics of the invention will become apparent by reading the following illustrative and unrestrictive examples.

Example 1

Demonstration of the Activity of the Peptides According to the Invention on Adipocytes Cell Culture:

Undifferentiated 3T3-L1 preadipocyte cell lines were seeded in 8-well Lab-Tek slides (for oil red staining), in 12-well plates (for ATP measurement), in 24-well plates (for cAMP measurement) and in 6-well plates (for glycerol measurement) as well as with DMEM culture medium (4.5 g/l) containing antibiotics. These 3T3-L1 preadipocytes were capable of entering, under certain conditions, the terminal differentiation phase.

Adipocyte Differentiation:

Once the 3T3-L1 cells had reached 100% confluence, they were differentiated by putting them into culture in various mediums, over a period of 6 to 8 days.

During the first 2 days, cells were cultured in the presence of IBMX, dexamethasone, and insulin diluted in DMEM culture medium at 4.5 g/l. Then, they were cultured for two days only in the presence of insulin diluted in DMEM culture medium at 4.5 g/l and, finally, the cells were cultivated for 2 to 3 days in culture medium containing exclusively DMEM 4.5 g/l.

Cell differentiation in mature adipocytes was visualized by the appearance of lipid droplets in the cytoplasm of the cells.

The effect of the peptide, as well as its impact on 3T3-L1 cells that are differentiated or in the process of differentiation was evaluated through various techniques:

Oil red staining,
Measurement of the quantity of intracellular ATP,
Measurement of the quantity of intracellular cyclic AMP,
Measurement of the quantity of glycerol released by the cells.

Oil Red Staining:

The principle of this evaluative test on the effect of peptides rests on a microscopic observation of the number and size of lipid vacuoles of adipocytes after staining. Adipocytes were incubated or not in the presence of the substance to be tested.

3T3-L1 cells, seeded in 8-well Lab-Teks, were treated with the peptide of SEQ ID NO:1, i.e. of sequence Pro-Leu-Asp-Thr-Ala-Lys-Val-Arg-Leu-Gln, representative of the peptide family according to the invention, placed in a 0.5% solution at 50 ppm. The active ingredient was added at various stages of culture:

At the start of the incubation and until the end of adipocyte differentiation (72 hours of culture until 100% confluence, then for the 6 days of differentiation);

6 hours after incubation and until the end of cell differentiation (66 hours of culture until 100% confluence, then for the 6 days of differentiation);

Once cells differentiated in the adipocytes, they were treated with the active ingredient for 6, 24, or 48 hours.

After these different incubation periods, in the presence or not of the active ingredient to be tested, 3T3-L1 were stained using the oil red staining technique. The oil red solution (Sigma, O-0625) was prepared by adding 0.5 g of the product to 100 ml of isopropanol and by making a 4/10 dilution of this solution in distilled water, followed by filtration. The cells were fixed for 10 minutes in a solution of 4% formol and NaCl, and the oil red solution was applied for 15 minutes. A 30 second counter-staining in Hematoxylin was possible. The cells were then rinsed with tepid water and mounted on slides in hydrophilic medium (Aquatex). Observation was carried out using an optical microscope in order to distinguish the adipose vacuoles stained in red.

The results of cell observation demonstrated that cells treated with the peptide well before the beginning of differentiation (i.e. at the start of incubation, or 6 hours after incubation) had a less round morphology and a clearly decreased content of intra-adipocyte lipid vesicles when compared with the control cells (to which the active ingredient was not applied). This same observation was also carried out through comparison with mature adipocytes, i.e. differentiated adipocytes, to which the active ingredient was applied, and which had a bulky spherical form and a significant accumulation of intracytoplasmic lipid vesicles.

The solution containing the peptide according to the invention thus turned out to be particularly efficient in adipocytes in the process of differentiation and not in mature adipocytes which already had accumulated triglycerides in their intra-adipocyte vesicles. Indeed, no reduction was observed when the active ingredient was applied once differentiation was completed.

Measurement of Intracellular cAMP:

The objective of this test was to measure the variation of the intracellular concentration of cAMP in adipocytes, in order to deduce a possible activation of the phenomenon of lipolysis.

The test was carried out on differentiated 3T3-L1 cells. These adipocytes were treated with the peptide of (SEQ ID NO: 1), i.e. of sequence Pro-Leu-Asp-Thr-Ala-Lys-Val-Arg-Leu-Gln, representative of the peptide family according to the invention, placed in a 0.5% solution at 50 ppm, for periods of 15 minutes, 30 minutes, or 1 hour. In parallel, differentiated 3T3-L1 cells were also treated with isoproterenol (an agent that induces lipolysis), at 1 μM, thus forming a positive control.

After the various incubation periods, in the presence of the active ingredient being tested or in the presence of isoproterenol, the quantity of cAMP contained in adipocytes was measured using the "AMP Biotrak® EIA System" kit purchased from Amersham Biosciences as well as by a test principle, colorimetric ELISA. The kit made cell lysis possible through a solution allowing for the hydrolysis of cellular membranes and the release of intracellular cAMP in the medium. Followed by the binding of antibodies specific to intracellular cAMP extracted from samples, which is placed in competition with cAMP that has been coupled to the enzyme, peroxidase. Thus, after revealing the reaction with the substrate TMB, the more cAMP there is in the samples to be measured, the weaker the signal will be.

The results obtained showed that, in the presence of the active ingredient, there was no increase in the intracellular quantity of cAMP in differentiated cells, compared to the control condition, i.e. compared to the cells treated with isoproterenol.

Measurement of Intracellular ATP:

The aim of this study was to determine the influence of the peptide according to the invention on the quantity of intracellular ATP. The study was carried out using an "ATP Bioluminescence Assay HS II" kit. Differentiated 3T3-L1 cells were treated with a 0.5% solution at 50 ppm, containing the peptide of SEQ ID NO: 1, representative of the peptide family according to the invention, for a period up to 96 hours. At the end of the incubation time, the wells were emptied of their medium and were rinsed with 2 ml of cold PBS before adding 250 μl of lysis buffer, provided by the kit. The cells were then scraped, and then collected separately in 14 ml tubes. Each well was rinsed with 2×500 μl of cold PBS and everything was again collected in the respective tubes. Each tube was then placed in the polytron for 10 seconds at 18000 rpm. From these samples, a dilution of 1/12000, using cold PBS, was carried out before each reading. ATP quantity assessment was performed on these samples: 50 μl of this dilution were placed in a luma-basin and 50 μl of luminol were added. The reading of luminescence started after 10 seconds. The values were standardized compared to the quantity of proteins for each sample. Measurements were taken using a Biocounter M2010A LUMAC®/3M.

Measurement of Glycerol:

The purpose of this study was to determine the influence of the peptide according to the invention on glycerol release by adipocytes, glycerol being the result of lipolysis.

Differentiated 3T3-L1 cells were treated with a 0.5% solution at 50 ppm, containing the peptide of SEQ ID NO:1, representative of the peptide family according to the invention, for periods of 1 h 30, 3 h, 5 h, 7 h and 24 h.

The concentration of glycerol was determined using a series of enzymatic reactions leading to the formation of NADH of which the produced quantity was evaluated by spectrophometric readings at 340 nm, the formation of NADH being proportional to the quantity of glycerol released in the culture medium. An internal control of 1 mM glycerol was also used. The values were standardized in comparison to the quantity of proteins for each sample.

The obtained results enabled us to note that in the various times studied, glycerol release by differentiated cells was identical for the control wells and the wells treated with the active ingredient at 0.5%.

Conclusions:

The results of the oil red staining test enabled us to conclude that the active ingredient according to the invention has a particularly efficient effect on the reduction of intra-adipocyte lipid droplet formation. However, this effect was only observed when the active ingredient was applied before the beginning and/or during cell differentiation, no reduction being observed when the active ingredient was applied to mature adipocytes. These results thus suggest that the peptide acts on lipogenesis and not on lipolysis.

The increases in the quantities of cAMP and intracellular ATP are indicators of the activation of the lipolysis pathway, the amount of cAMP regulating Triglyceride-lipase activity, and the enzyme allowing triglyceride hydrolysis. Thus, the lack of increase in the amounts of cAMP and intracellular ATP suggest that the active ingredient according to the invention does not act by increasing the phemonenon of lipolysis. In addition, these results were confirmed by the non-increase in glycerol release in the extracellular medium, glycerol being a product of lipolysis.

These results thus tended to demonstrate that the peptides according to the invention possess a truly efficient action on adipocytes, and that they prove to be particularly efficient in the process of limiting adipocyte hypertrophy.

The active ingredient according to the invention thus prevents the accumulation of lipid droplets in adipocytes, and allows therefore, more or less directly, a reduction in adipose mass and an inhibition of its development.

This reduction of lipid vacuoles in non-mature adipocytes, combined with the results of cAMP, ATP and glycerol assays, makes it possible to conclude that the peptides according to the invention act, at the level of adipocytes, on the mechanism of lipogenesis and not on the mechanism of lipolysis. The peptides according to the invention thus promote the non-accumulation of triglycerides contained in intra-adipocyte vesicles.

Example 2

Preparation of Compositions

1. Slimming Cream

| Commercial Names | INCI Names | % mass |
|---|---|---|
| PHASE A | | |
| MONTANOV 68® | Cetearyl Alcohol (and) Cetearyl Glucoside | 5.00 |
| Squalane | Squalane | 2.50 |
| DUB IPP | Isopropyl Palmitate | 3.50 |
| EUTANOL G® | Octyldodecanol | 1.50 |
| PHENONIP® | Phenoxyethanol (and) Methylparaben (and) Ethylparaben (and) Butylparaben (and) Propylparaben (and) Isobutylparaben | 0.50 |
| PHASE B | | |
| Demineralized water | Aqua (Toilets) | qs |
| Glycerine | Glycerin | 3.00 |
| Butylene Glycol | Butylene glycol | 3.00 |
| PHASE C | | |
| SIMULGEL EG® | Sodium Acrylate/Acryloyldimethyl Taurate Copolymer (and) Isohexadecane (and) Polysorbate 80 | 0.60 |
| PHASE D | | |
| Peptide SEQ ID NO: 1 | | 1.25 ppm |
| Perfume | Perfume (Fragrance) | qs |
| Colorant | | qs |

The components of phase A are melted at 75° C. and the components of phase B are heated at 75° C. Phase A is emulsified with B, then the mixture is cooled to below 40° C. Phases C and D are then added under continuous agitation.

2. Firming—Slimming Spray

| Commercial Names | INCI Names | % mass |
|---|---|---|
| PHASE A | | |
| EMULGADE SEV® | Glyceryl Stearate (and) Ceteareth-20 (and) Ceteareth-12 (and) Cetearyl Alcohol | 4.60 |
| EUMULGIN B2® | Ceteareth-20 | 1.40 |
| CETIOL OE® | Dicaprylyl Ether | 3.00 |
| DUB B1215 | C12-C15 Alkyl Benzoate | 5.00 |
| PHENONIP® | Phenoxyethanol (and) Methylparaben (and) Ethylparaben (and) Butylparaben (and) Propylparaben (and) Isobutylparaben | 0.50 |
| DUB ININ | Isononyl Isononanoate | 5.00 |
| PHENONIP® | Phenoxyethanol (and) Methylparaben (and) Ethylparaben (and) Butylparaben (and) Propylparaben (and) Isobutylparaben | 0.50 |
| PHASE B | | |
| Demineralized water | Aqua (Toilets) | 15.00 |
| Glycerine | Glycerin | 3.00 |
| PHASE C | | |
| Demineralized water | Aqua (Toilets) | qs |
| PHASE D | | |
| Peptide SEQ ID NO: 1 | | 1.50 ppm |
| Perfume | Perfume (Fragrance) | qs |
| Colorant | | qs |

The components of phase A and phase B are heated separately at 65° C.; phase B is incorporated into phase A under agitation. The temperature of the mixture is increased to 83° C. then it is cooled until it reaches a temperature of phase inversion. Phase C is then added. The active ingredient is incorporated when the temperature reaches less than 40° C. It is then possible to add perfumes and/or dyes.

3. Firming—Slimming—Anti-Cellulite Gel

| Commercial Names | INCI Names | % mass |
|---|---|---|
| CARBOPOL ULTREZ® 10 (2%) | Carbomer | 25.00 |
| Demineralized water | Aqua (Toilets) | qs |
| DUB DIOL | Methyl Propanediol | 3.00 |
| EDTA | Tetrasodium EDTA | 0.10 |
| Glydant Plus Liquid | DMDM Hydantoïn (and) Iodopropynyl butylcarbamate | 0.20 |
| Peptide SEQ ID NO: 1 | | 1.25 ppm |
| TEA | Triethanolamine | 0.50 |
| Perfume | Perfume (Fragrance) | qs |
| Water-soluble colorant | | qs |

Carbopol gel is prepared at 2%. The ingredients are added in the order listed above, under agitation. The mixture is then neutralized with TEA. The perfume and dyes are added if necessary.

The invention claimed is:

1. A composition comprising a protein fragment of the uncoupling protein (UCP) family as an active ingredient, wherein the protein fragment is a synthetic peptide of the following formula:

(AA)n-Pro-X1-X2-X1-X3-Lys-X1-Arg-X4-X5-(AA)n
(SEQ ID NO: 10), wherein

X1=Leu, Thr, or Val,
X2=Asp, or Glu,
X3=Ala, or Val,
X4=Leu, Phe, or Tyr,
X5=Gln, Ile, or Met,
(AA) is any amino acid, and
n is a whole number ranging from 0 to 2;
and wherein said protein fragment comprises a synthetic peptide selected from the group consisting of:

1) Pro Leu Asp Thr Ala Lys Val Arg    (SEQ ID NO: 1)
   Leu Gln,

2) Pro Thr Glu Val Ala Lys Val Arg    (SEQ ID NO: 2)
   Phe Gln,

3) Pro Thr Asp Val Ala Lys Val Arg    (SEQ ID NO: 3)
   Leu Gln,

4) Pro Thr Glu Val Ala Lys Val Arg    (SEQ ID NO: 4)
   Leu Gln,

5) Pro Thr Asp Val Ala Lys Val Arg    (SEQ ID NO: 5)
   Phe Gln,

6) Pro Val Asp Val Val Lys Thr Arg    (SEQ ID NO: 6)
   Phe Ile,

7) Pro Val Asp Val Val Lys Thr Arg    (SEQ ID NO: 7)
   Tyr Met,

8) Pro Val Asp Val Val Lys Thr Arg    (SEQ ID NO: 8)
   Phe Met, and

9) Pro Val Asp Val Val Lys Thr Arg    (SEQ ID NO: 9)
   Tyr Ile.

2. The composition according to claim 1, wherein the peptide is Pro-Leu-Asp-Thr-Ala-Lys-Val-Arg-Leu-Gln (SEQ ID NO: 1).

3. The composition according to claim 1, wherein the peptide has at least one functional group protected by a protective group, the protective group being either an acylation or an acetylation of the amino terminal end, or an amidation or an esterification of the terminal carboxyl end, or both.

4. The composition according to claim 1, wherein the protein fragment is present, in the composition, in a concentration ranging from approximately 0.05 to 500 ppm compared to the total weight of the final preparation.

5. The composition according to claim 1, wherein the protein fragment is solubilized in one or more cosmetically or pharmaceutically acceptable solvent.

6. The composition according to claim 1, wherein the protein fragment is solubilized in, or fixed on, a cosmetically or pharmaceutically acceptable vector.

7. The composition according to claim 1, wherein said peptide is present in an amount sufficient to treat cellulite and/or orange-peel skin; and/or in order to reduce, eliminate, or prevent excess subcutaneous fat.

8. A cosmetic and/or dermatological and/or pharmaceutical composition comprising, in an acceptable medium, as an active ingredient, at least one said peptide as defined in the composition of claim 1.

9. The composition according to claim 7, wherein said composition is in the form of a cosmetic and/or dermatological composition adapted for cutaneous topical administration and includes a cosmetically or pharmaceutically acceptable medium.

10. The composition according to claim 8, wherein said composition is in the form of an aqueous or hydro-alcoholic solution.

11. A process of cosmetic care to reduce excess subcutaneous fat, and/or to reduce cellulite, and/or to reduce the phenomenon of orange-peel skin, said process comprising administering to the surface of the skin of a subject an effective quantity of the composition defined according to claim 8.

12. A process for treating excess subcutaneous fat, cellulite, or orange-peel skin, comprising administering to the skin of a subject in need thereof an effective amount of the composition according to claim 1.

13. The composition according to claim 4, wherein the protein fragment is present, in the composition, in a concentration ranging from approximately 0.1 to 50 ppm compared to the total weight of the final preparation.

14. The composition according to claim 5, wherein said one or more cosmetically or pharmaceutically acceptable solvent is selected from the group consisting of water, ethanol, propylene glycol, butylene glycol, dipropylene glycol, ethoxylated or propoxylated diglycols, cyclic polyols, vaseline, a vegetable oil, and any mixture of these solvents.

15. The composition according to claim 6, wherein said cosmetically or pharmaceutically acceptable vector comprises a liposome.

16. The composition according to claim 6, wherein the protein fragment is absorbed on powdery organic polymers, mineral supports, talcs or bentonites.

17. The composition according to claim 8, wherein said composition is in the form of an oil solution or emulsion chosen from oil-in-water emulsions, water-in-oil emulsions, or multiple emulsions.

18. The composition according to claim 8, wherein said composition is in the form of creams, suspensions, or powders, wherein said composition can also be more or less fluid or solid and can take the form of creams, lotions, milks, serums, ointments, gels, pastes, mousse, or sticks.

19. The composition according to claim 1, wherein the protein fragment comprises one or more pseudo-peptide bond.

20. The composition according to claim 1, wherein the protein fragment comprises one or more amino acid in the D and/or L configuration.

21. The composition according to claim 8, wherein the composition further comprises at least one additional active agent.

22. The composition according to claim 21, wherein the at least one additional active agent is capable of promoting lipolysis.

23. The composition according to claim 1, wherein the synthetic peptide is obtained by chemical synthesis.

* * * * *